United States Patent
Gevorgyan

(10) Patent No.: US 12,402,914 B2
(45) Date of Patent: Sep. 2, 2025

(54) METHOD OF DEEP CLEANSING OF SKIN

(71) Applicant: Armen Gevorgyan, Yerevan (AM)

(72) Inventor: Armen Gevorgyan, Yerevan (AM)

( * ) Notice: Subject to any disclaimer, the term of this patent is extended or adjusted under 35 U.S.C. 154(b) by 15 days.

(21) Appl. No.: 17/757,989

(22) PCT Filed: May 31, 2021

(86) PCT No.: PCT/IB2021/054738
§ 371 (c)(1),
(2) Date: Jun. 24, 2022

(87) PCT Pub. No.: WO2022/195334
PCT Pub. Date: Sep. 22, 2022

(65) Prior Publication Data
US 2024/0188991 A1 Jun. 13, 2024

(30) Foreign Application Priority Data
Mar. 19, 2021 (AM) ................................ 20210023Y

(51) Int. Cl.
| | |
|---|---|
| *A61K 36/00* | (2006.01) |
| *A61B 17/54* | (2006.01) |
| *A61B 42/10* | (2016.01) |
| *A61K 8/9789* | (2017.01) |
| *A61K 8/9794* | (2017.01) |
| *A61K 8/98* | (2006.01) |
| *A61Q 19/10* | (2006.01) |
| *A61B 17/00* | (2006.01) |
| *A61B 17/32* | (2006.01) |

(52) U.S. Cl.
CPC .............. *A61B 17/54* (2013.01); *A61B 42/10* (2016.02); *A61K 8/9789* (2017.08); *A61K 8/9794* (2017.08); *A61K 8/986* (2013.01); *A61K 8/988* (2013.01); *A61Q 19/10* (2013.01); *A61B 2017/00761* (2013.01); *A61B 2017/320004* (2013.01); *A61K 2800/28* (2013.01)

(58) Field of Classification Search
CPC ..................................................... A61K 36/87
See application file for complete search history.

(56) References Cited

U.S. PATENT DOCUMENTS 4,117,172 A * 9/1978 Bradshaw ............ A23B 7/0056
426/573

FOREIGN PATENT DOCUMENTS

| AM | 20210023 Y | 3/2021 |
|---|---|---|
| CN | 1176825 A | 3/1998 |
| CN | 107488552 A | 12/2017 |
| CN | 110799174 A | 2/2020 |
| RU | 2191000 C2 | 10/2002 |
| RU | 2314085 C2 | 1/2008 |
| RU | 2336883 C2 | 10/2008 |
| RU | 2328324 C2 | 7/2009 |
| RU | 2414878 C1 | 8/2009 |
| RU | 2659026 C1 | 6/2018 |
| WO | 2019/022997 A1 | 1/2019 |

OTHER PUBLICATIONS

International Search Report in International Application No. PCT/IB2021/054738 mailed on Oct. 21, 2021.
Written Opinion of the International Searching Authority in International Application No. PCT/IB2021/054738 mailed on Oct. 21, 2021.
Abdrabba Salem et al. Chemical composition of pulp, seed and peel of red grape from libya. Global Journal of Scientific Researched. 2015, vol. 3(2), p. 6-11.
Traditional Knowledge Resource—Kaiyadeva Nighantuh (Pathya Apathya Vibodhakah) 1979 Najmul Ghani Khan Najmi Rampuri p. 31.
Traditional Knowledge Resource—Khazaain-al-Advia.—vol. I. 1911. Mohammad Najmul Ghani Khan p. 625.
Georgian IP Office Search report and Written opinion in case No. 15876/1, dated Feb. 20, 2023.
EA search report in Application No. 202200015 dated Oct. 18, 2022.
EP Supplementary Search Report in Application No. EP 21931385 dated Jul. 28, 2023.
Third Party Observations for Application No. EP20210931385 dated Aug. 8, 2023.
Traditional Knowledge Resource—Muheet Azam—vol. I. 1896 AD Mohammad Azam, p. 225.

(Continued)

*Primary Examiner* — Qiuwen Mi
(74) *Attorney, Agent, or Firm* — Phil IP Law Inc.; Narek Zohrabyan; Karen Kirk Galoyan

(57) ABSTRACT

The present invention relates to aesthetic cosmetology and physiotherapy, particularly, to the method of deep cleansing of skin using grapes and wine's steam. It's also useful for skin anti-aging, getting rid of overweight and cellulite, removing harmful substances.

The skin is pre-cleansed with wine steam, then peeling is done. Peeling is carried out in steps. In the first step, chemical peeling is performed at a temperature of 50-85° ° C. for 30-45 minutes in the steam cabin by steaming the patient's body with a steam mixture that consists of wine steam containing active substances which is obtained by getting in contact with medical herbs.

In the second step, mechanical peeling is carried out with a special puree, which contains the following components, wt. %. alcohol-free hot wine—10-30, ground dry grape seed—2.5-10, freshly ground grape—10-30, grape seed oil—1-5 and hot water up to 1 kg.

5 Claims, No Drawings

(56) References Cited

OTHER PUBLICATIONS

Traditional Knowledge Resource—Al-Jaame Li-Mufradat Al-Adviya Wal-Aghziya—vol. IV. 1874 AD Ziyauddin Abdullah bin Ahmad Al-Undulisi, p. 57.
Traditional Knowledge Resource—Khazain-Ul-Adviya 1979 Acharya Priyavrat Sharma and Dr. Guru Prasad Sharma p. 389.
French Grape Seed Refining Body Scrub.
Grape Wine Facial Kit.
Grape Seed Peeling.

\* cited by examiner

METHOD OF DEEP CLEANSING OF SKIN

TECHNICAL FIELD

The present invention relates to aesthetic cosmetology and physiotherapy, particularly, to the method of deep cleansing of skin using grapes and wine's steam.
The method is also useful for skin anti-aging, getting rid of excess weight and cellulite, removing harmful substances and toxins from the organism and keeping the body fresh.

BACKGROUND ART

The Jewish Talmud noted wine to be "the foremost of all medicines: wherever wine is lacking, medicines become necessary."

For centuries wine was known as an appetizing, alcoholic beverage, which also improves digestion and mood. But thousands of years ago it was also known for its healing and aesthetic properties.

In Homer's Iliad doctors named Mahao and Padalia were mentioned, who were healing scars with wine. Hypocrite pointed out wine's healing properties in his works numerous times.

In the second century A.D. surgeon Galen was assigned to take care of wounded gladiators. Galen was using wine during surgeries as an antibacterial and a pain killer. There were no deaths during his treatment. That magical beverage was able to heal even those giants.

It is known that the ancient Romans were adding young red wine to their baths for smooth and beautiful skin.

Ancient Greeks also knew about red wine's rejuvenating ability. They were mixing wine with grass extract and massaging it into the skin and it left them with perfect skin tone and body shape.

Various methods are known of skin treatments, to activate the renovation of skin, to prevent untimely aging of skin, to improve the aesthetic and functional parameters of the skin.

For example, patent RU 2314085, A61H 33/06, 2007 discloses the method of physiotherapy, physiotherapy equipment, steam physiotherapy, according to which, biologically active substances are prepared and used in a steam room at 30-80° C.

The disadvantage of that method is that it's complicated and takes longer. It doesn't provide deep cleansing of the skin.

Patent RU 2328324, A61Q 19/00, 2008 discloses how to eliminate cosmetic skin imperfections, according to which it includes sequential cleansing of the skin, nourishment, hydration and protection of the skin from negative external factors: and deep cleansing of the skin is ensured by covering the skin with a complex effect mask.

The method of physiotherapeutic influence is also known, according to which they put the patient in a steam room and leave the patient's head outside. Then, the patient is treated with a mixture of steam-aerosol herbs (Patent RU 2414878, A61G 10/02, 2011).

The disadvantage of this method is that it does not provide an active effect on the cleansing of the pores and penetration of healing substances through the pores and therefore, does not perform deep cleansing of the skin.

There are currently three main types of skin cleansing methods: mechanical peelings, chemical peelings, and enzymatic peelings.

During mechanical peelings, small grains or brushes are used to scrape off dead skin. Mixtures with different ingredients are used, which contain harmful chemicals. This method is certainly very harsh for the skin, it can easily irritate sensitive skin, and it's strictly contraindicated for skin types that are prone to acne.

Chemical peelings are mainly performed with alpha-hydroxy and beta-hydroxy acids. Beta-hydroxy acids are dangerous in case of direct contact with the skin, and require strict supervision by a specialist. Otherwise, they can cause chemical burns, scars, rashes, and hyperpigmentation. They are strictly contraindicated in pregnancy.

Alpha-hydroxy acids are more sensitive, safer, more compatible with different skin types, and not contraindicated in pregnancy. However, in direct contact with the skin, they are not able to penetrate into the deep layers of the skin and the result is not visible.

Enzymatic peeling is the mildest and most natural method. Enzymes break down skin keratin like chemical peelings, performing slower and providing softer skin repair. However, for visible results, the process needs to be repeated many times. (Beauty Forum 2009 (7), 56-58, Hill r.n., Pamela (2006). *Milady's Aesthetician Series. Peels and Peeling Agents*):

In modem medicine wine therapy—enotherapy is developing rapidly as a new field. Grapes contain polyphenols, substances that block free radicals. Free radicals occur in the human body because of Ultra Violet (UV) rays, pollutants in the environment, and tobacco use. They destroy cells, prevent the formation of new cells, and, in general, age the body. Polyphenols act like traps for radicals. Among these substances, grapes and wine also contain resveratrol, which is also called the "secret of youth" sitting under a wine bottle. It has antioxidants, anti-inflammatory properties, helps prevent enlargement of the lymph nodes, liver, stomach, breast tumors, skin cancer, leukemia. It also reduces the risk of cardiovascular and digestive diseases, atherosclerosis. It also protects the body from UV radiation. (Paul B., Masih I., Charpentier C. *Occurrence of Resveratrol and Pterostilbene In Age-Old Darakchasava. An Ayurvedic Medicine from India*. Journal of Ethnophamacology. 1999):

DISCLOSURE OF THE INVENTION

The aim of the invention is to develop a method of mending cosmetic imperfections of the skin, prevention of age changes and deep cleansing of the skin, excluding skin damage, increase the efficiency of the method of active penetration of healing substances through the skin pores, as well as the positive effects of wine steam.

The essence of the invention is that in the method of deep cleansing of the skin, it is pre-cleansed with wine steam, and then peeling is performed. According to the invention, peeling is carried out in steps.

In the first step, chemical peeling is performed at a temperature of 50-85° ° C. for 30-45 minutes in a steam chamber by exposing the patient's body with a steam mixture that consists of wine steam containing active substances which is obtained by infusing the wine with medical herbs.

In the second step, mechanical peeling is carried out with a special puree, which contains the following components, percent by weight {wt. %}. Alcohol-free hot wine—10-30, ground dry grape seed—2.5-10, freshly ground grape—10-30, grape seed oil—1-5 and hot water up to 1 kg.

DETAILED DESCRIPTION OF THE INVENTION

The present invention will now be described in detail.
The invention is carried out in two steps.
The first step's chemical peeling's advantages are the following:
  steam has a higher temperature (75-85° C.), which allows faster, more efficient, full penetration of wine into the skin. The steam makes skin delicate, and the tartaric acid, exfoliates the epidermis, by interacting with the proteins of the epidermis, and promotes the rapid and deep removal of dead cells.
  at high temperatures, tartaric acid changes the pH of the skin to acidic, dilating the vessels and increasing the permeability of the vessels, promoting more intensive penetration of all the useful substances in the wine into the blood.
  tartaric acid in wine steam stimulates sweat production, removal of toxins from the body and breakdown of fats.
  tartaric acid in wine steam, which is an alpha-hydroxy acid that doesn't have the negative effects of beta-hydroxy acids, at higher temperatures even more widens skin pores and promotes its deeper penetration into the skin, and hydrogen cations in the tartaric acid play a catalytic role in the fat breakdown: promoting rapid removal of excess weight and cellulite.
  the tanning agents in wine penetrate deeper into the skin at high temperatures, and increase its elasticity, making the skin glow.

Second Step:
  already exfoliated skin makes the next step—mechanical peeling—more effective and safer.
  mechanical peeling is performed with a special puree with the following quantitative and qualitative composition: alcohol eliminated/non-alcoholic hot wine (10-30%), ground dry grape seed (2.5-10%), freshly ground grape (10-30%), grape seed oil (1-5%) and hot water up to 1 kg.
  the wine in the puree with—its tartaric acid—continues its cleansing effects through rubbing it onto the skin.
  wine contains tartaric acid, which is an alpha-hydroxy acid. It is behind many healthy properties of wine. It has anti-inflammatory and anti-fungal properties. It stimulates the synthesis of collagen and elastin. It is these proteins that give the skin elasticity. In addition, grapes contain all 20 amino acids necessary for the development of human cells, as well as 350 chemical compounds and microelements, such as magnesium, iron, chromium, zinc, rubidium, for bioactivity of human cells,
  finally, ground dried grape seeds effectively and safely remove dead cells of the already exfoliated skin while also transferring their useful substances from the skin into the body.
  grape seed oil to some extent diminishes friction caused by mechanical peeling that uses ground dried grape seeds. Thus, the procedure is more comfortable and, at the same time, the powerful supply of vitamin A and E are transferred to the skin; promoting the development of a healthier skin.
  ground grapes also somewhat diminish friction caused by mechanical peeling that uses ground dried grape seeds. At the same time, ground grapes contain tartaric acid, resveratrol, and other polyphenols, which also help to cleanse the skin.
  freshly ground grapes, which are an ingredient of the mechanical peeling puree, contain many enzymes, coenzymes, which have a milder but very effective influence on the cells of the skin that has already been chemically and mechanically peeled, and also contribute to the effective removal of dead skin cells.

The invention differs from the currently known skin cleansing methods by the fact that it is recommended to use all the methods together using only natural ingredients (grapes and wine), and most importantly, in a very precise sequence of steps, as each previous step prepares the skin for the next stage with maximum effectiveness for getting a visible result.

EXAMPLES

The following is an example of the invention.
Expose steam to the body with wine vapors as follows.
Under the wooden planks (mostly pine) of an individual steam chamber, install two electric, temperature-adjustable plates. The plates having placed on them stainless steel containers with a diameter of about 40 cm, in which 2 liters of wine (red or white) are poured. The containers should be wide and low profile so that the wine is spread over a large area in a thin layer for purposes of boiling quickly.

The plates are turned on 10-15 minutes before the start of the procedure, at the highest temperature, such that the wine starts to boil and evaporate. The lid of the steam chamber is opened, the client lies on the wooden planks so that after closing the lid, the head of the client stays out of the opening made on one of its lateral surfaces. The towel is placed between the opening and the neck, thus creating a completely enclosed space in the chamber. Before starting the procedure. The wine boils for 15 minutes under the maximum temperature and produces a large amount of steam, which completely fills the cavity of the chamber. Then, the temperature of the plates are lowered for the next 15 minutes, although making sure that the wine does not stop boiling. Lowering of the temperature decreases the temperature in the chamber to make the procedure more tolerable.

By massaging the face with cold water or ice, the procedure becomes more tolerable and pleasant. During the last five minutes, the towel (previously placed between the neck and chamber opening) is placed above the head, allowing the wine vapors to steam the face and the upper respiratory tract, as the client inhales the vapors.

To broaden the range of key properties of wine vapor described above, mixtures of various plant collections or biologically active substances (herbs) are used with wine. For example, in order to obtain anti-bacterial and anti-inflammatory effect. 1.0 liter of wine is mixed with 25-50 g of chamomile along with violet petals, pansy petals and rose petals. In order to reduce the oil level of the skin. 1 liter of wine is mixed with 20-30 g of dried lemon and orange peels, *Achillea millefolium*, and saffron. For dry skin. 1 liter of wine is mixed with 20-30 g of mint and jasmine are mixed. To tighten the skin. 30-50 g of tea, chamomile, orange peel, calendula, saffron are mixed with 1 liter of wine. For dry skin. 1 liter of wine is also mixed with 200-250 g of oily (3-3.5% fat) milk, and for oily skin, 1 liter of wine is mixed with 1 tablespoon of honey.

To steam the face, a separate face steamer is used with wine diluted with water.

After steaming, in the initial stage, the specialist performs mechanical peeling of the already exfoliated skin with special gloves (rough, uneven cloth) to remove dead skin cells. Lymphatic drainage is provided with proper movements.

Then, the specialist spreads the peeling puree on the client's body with special movements with bare hands and fingers, thus scrubbing and exfoliating using the thicker part of the puree. Finally, the specialist rinses the area of the skin with the viscous part of the peeling puree, as he continues the scrubbing.

The invention of the use of grapes and wine vapors in the above-mentioned method is currently widely used in Wine and Grapes SPA belonging to "Anmage" LLC. In addition to steaming the whole body with wine vapors in an individual steam chamber (the body is peeled with the above-mentioned puree) the hydro massage/jacuzzi with the wine, classic body massage with grape seed oil, facial, foot, hand skin cleansing, and rejuvenating procedures with wine and grapes are also done in Wine and Grapes SPA belonging to "Anmage" LLC.

So, the announced invention differs from the known methods by using the currently known skin cleansing methods together in one single procedure, using only natural substances, and wine vapors as a chemical peeling substance, which penetrates much more intensely from the skin to the body (as opposed to bath and rub method) as a mechanical peeling material: ground grapes, grape seeds, grape seed oil, as an enzymatic peeling material—enzymes in grapes which, contrary to chemicals, are more effective and harmless. This method also differs by using substances that not only help to cleanse the skin, but also all the substances found in wine and grapes necessary for the vital activity of the organism pass through the skin into the blood throughout the body, contrary to the use of these substances by drinking or eating. During absorption into the bloodstream, most of these substances are broken down in the liver.

The invention claimed is:

1. A method of using a puree mix to deep clean skin, comprising:
    pretreating a skin by exposing the skin to a wine vapor;
    mechanically peeling the skin using gloves to scrub dead skin cells;
    mechanical and enzymatic peeling the skin by applying a high viscosity part of the puree mix, which contains enzymes and coenzymes derived from grapes, unto the skin and scrubbing and exfoliating the skin with movements using bare hands; and
    mechanically peeling the skin by rinsing the skin with a low viscosity part of the puree mix as further scrubbing and exfoliating continues.

2. The method of claim 1, wherein the pretreating of the skin includes exposing the skin to the wine vapor at a temperature range of between 50-85 centigrade.

3. The method of claim 1, wherein the pretreating of the skin includes exposing the skin to the wine vapor for a duration of between 30-45 minutes.

4. The method of claim 2, wherein the wine vapor is first infused with ingredient(s) selected from the group consisting of:
    a. chamomile, violet petals, pansy petals and rose petals;
    b. dried lemon and orange peels, achillea millefolium, and saffron;
    c. mint and jasmine;
    d. tea, chamomile, orange peel, calendula, and saffron;
    e. milk; and
    f. honey.

5. The method of claim 1, wherein the puree mix is made by mixing non-alcoholic hot wine, ground dry grape seeds, freshly ground grapes, grape seed oil and hot water.

* * * * *